US00PP37390P2

(12) United States Plant Patent
Bazak

(10) Patent No.: US PP37,390 P2
(45) Date of Patent: Apr. 28, 2026

(54) GRAPEVINE PLANT NAMED 'BIG BEAR'

(50) Latin Name: ***Vitis vinifera* L.**
Varietal Denomination: Big Bear

(71) Applicant: Bazak Agro Innovation Ltd, Carmei Yossef (IL)

(72) Inventor: Hanan Bazak, Carmei Yossef (IL)

(73) Assignee: Bazak Agro Innovation Ltd, Carmei Yossef (IL)

( * ) Notice: Subject to any disclaimer, the term of this patent is extended or adjusted under 35 U.S.C. 154(b) by 0 days.

(21) Appl. No.: 19/254,983

(22) Filed: Jun. 30, 2025

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 5/0812
See application file for complete search history.

(56) References Cited

U.S. PATENT DOCUMENTS

PP4,077 P 7/1977 Anderson

*Primary Examiner* — Kent L Bell
(74) *Attorney, Agent, or Firm* — Foley & Lardner LLP

(57) ABSTRACT

A new and distinct Grapevine plant of *Vitis vinifera* named 'Big Bear', which has demonstrated that the combination of characteristics as herein disclosed for the new variety are firmly fixed and retained through successive generations of asexual propagation. The new variety is primarily adapted to the growing conditions in full sunlight grown in a Mediterranean, hot summer climate. The new variety is particularly characterized by early to mid-season ripening with very large broad ellipsoid, green-yellow coloring, seedless berry ripening with some rudimentary seeds.

4 Drawing Sheets

Figure 1:
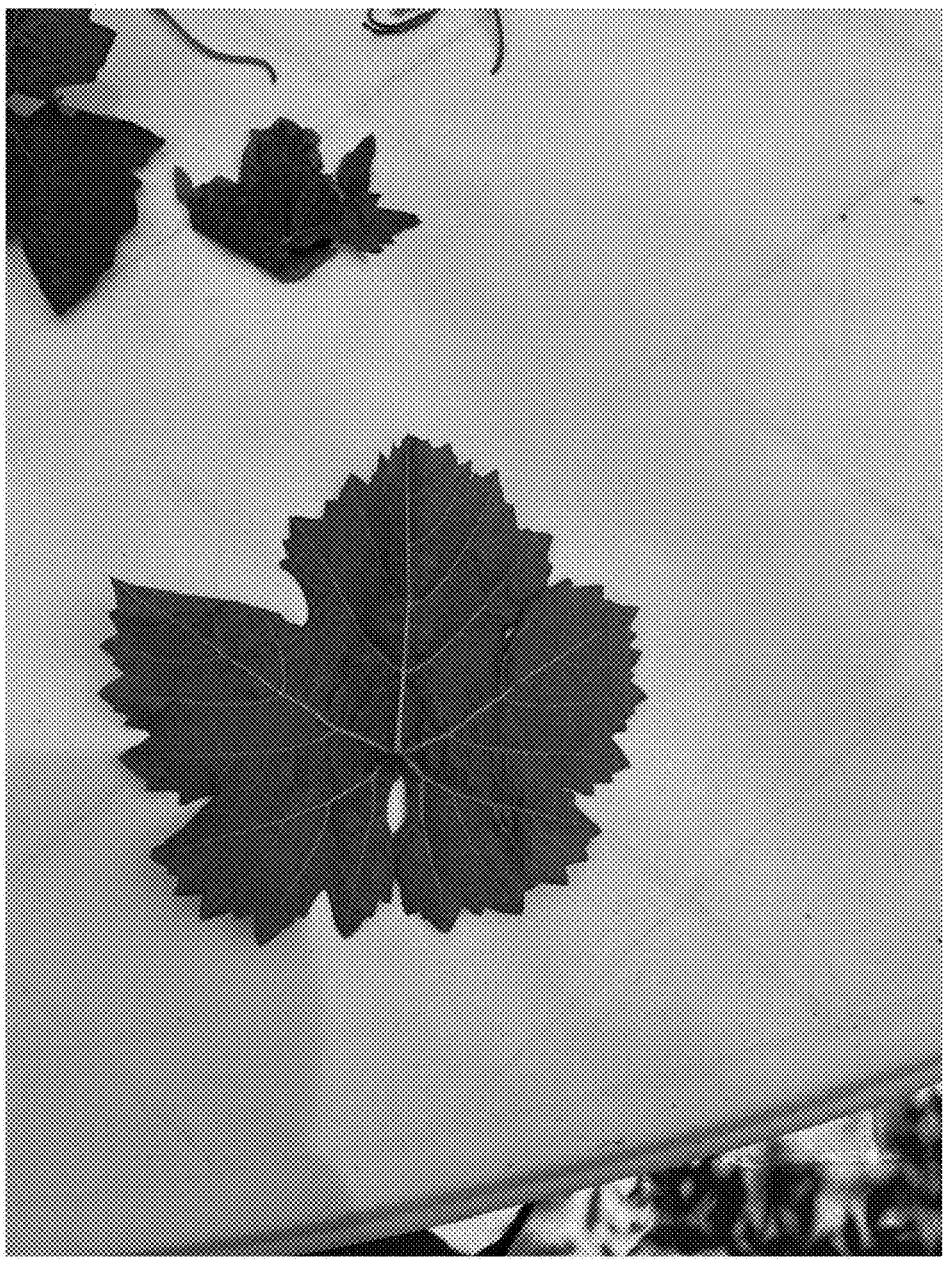

Botanical name of the genus and species of the plant claimed: *Vitis vinifera* L.

Variety denomination: 'Big Bear'.

BACKGROUND OF THE INVENTION

The present invention relates to a new and distinct variety of Grapevine plant, botanically known as *Vitis vinifera* of the Family Vitaceae, and hereinafter referred to by the variety denomination 'Big Bear'.

The new variety 'Big Bear' is a product of a planned breeding program conducted by the inventor Hanan Bazak, in Karmei Yossef, Gezer region in HaShephelah, Latitude 31.8480° N, Longitude 34.9213° E, Israel. The objective of the breeding program was to develop a new *Vitis vinifera* variety with a large, seedless, early to medium ripening, easy detachable juicy berry with excellent slightly muscat taste and with low susceptibility to Grape Sour Rot.

The new *Vitis vinifera* variety originated from a cross made by the inventor in 2012 in Karmei Yossef, Gezer region in HaShephelah, Israel. The female or seed parent is the *Vitis vinifera* own breeding line designated 'H 1352', (unpatented). The male or pollen parent is the *Vitis vinifera* own breeding line designated 'H 8351', (unpatented). The new *Vitis vinifera* 'Big Bear' was observed and selected by the inventor within the progeny of the stated cross in a controlled environment in 2012 in Karmei Yossef, Gezer region in HaShephelah, Israel.

Asexual propagation of the new *Vitis vinifera* variety by rooting of cuttings was first performed in 2018 and the final selection was made in 2024 in Karmei Yossef, Gezer region in HaShephelah, Israel, and has demonstrated that the combination of characteristics as herein disclosed for the new variety are firmly fixed and retained through successive generations of asexual propagation. The new variety propagates true-to-type.

BRIEF DESCRIPTION OF THE INVENTION

The following traits have been repeatedly observed and are determined to be characteristics of 'Big Bear' which in combination distinguish this Grapevine plant as a new, unique and distinct variety:

1. Berry ripening time: early to mid-season.
2. Berry shape: broad ellipsoid.
3. Berry skin color: green-yellow.
4. Berry flesh flavor: occasionally slightly muscat.
5. Berry seed formation: mainly seedless with some rudimentary seeds.

In comparison to the parental varieties, 'H 1352' (unpatented) and 'H 8351' (unpatented) 'Big Bear' differs primarily in the traits listed in Table 1.

TABLE 1

Comparison with Parent Varieties

| Characteristic | New Variety 'Big Bear' | Female Parent 'H 1352' (unpatented) | Male Parent 'H 8351' (unpatented) |
|---|---|---|---|
| Berry ripening time | Early to mid-season | Mid-season | Mid-season to late |
| Berry shape | Broad ellipsoid | ovoid | elongated |
| Berry skin color | Green-yellow | yellow | yellow |
| Berry flesh flavor | occasionally Slightly muscat | none | fruity |

Of the many well-known commercial varieties known to the present inventor, the most similar in comparison to the new *Vitis vinifera* 'Big Bear' is an unnamed *Vitis vinifera* grapevine plant of the Thompson Seedless class (U.S. Plant Pat. No. 4,077), which differs from the new Grapevine 'Big Bear' in the characteristics described in Table 2:

TABLE 2

Comparison with a Well-Known Commercial and Most Similar Variety

| Characteristic | New Variety 'Big Bear' | Comparison Variety Unnamed grapevine plant of the Thompson Seedless class (U.S. Plant Pat. No. 4,077) |
|---|---|---|
| Berry ripening time | Early to mid-season | Early |
| Berry shape | Broad ellipsoid | Long oval |
| Berry flesh flavor | Occasionally slight muscat | none |

BRIEF DESCRIPTION OF THE PHOTOGRAPHS

The accompanying photographs illustrate the overall appearance of the new *Vitis vinifera* variety 'Big Bear' showing the colors as true as is reasonably possible with colored reproductions of this type. Photographs were taken in 2024 of 10-year-old plants in the vineyard in Karmei Yossef, Gezer region in HaShephelah, Israel. Colors in the photographs may differ slightly from the color values cited in the detailed morphological description, which accurately describe the color of 'Big Bear'.

FIG. 1—shows a typical leaf of 'Big Bear'.

Figure 2:
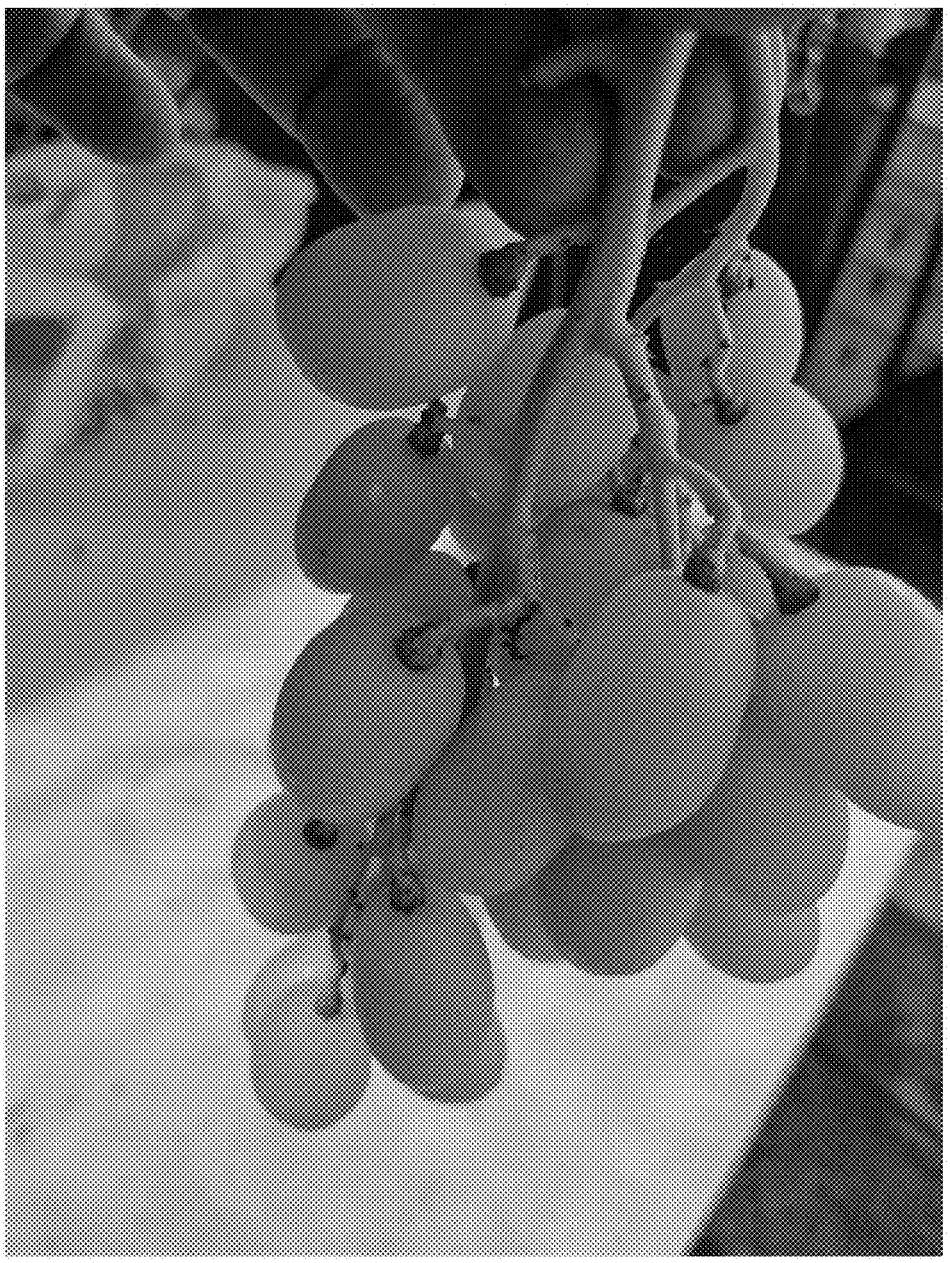

FIG. 2—shows a typical bunch of 'Big Bear'.

Figure 3:
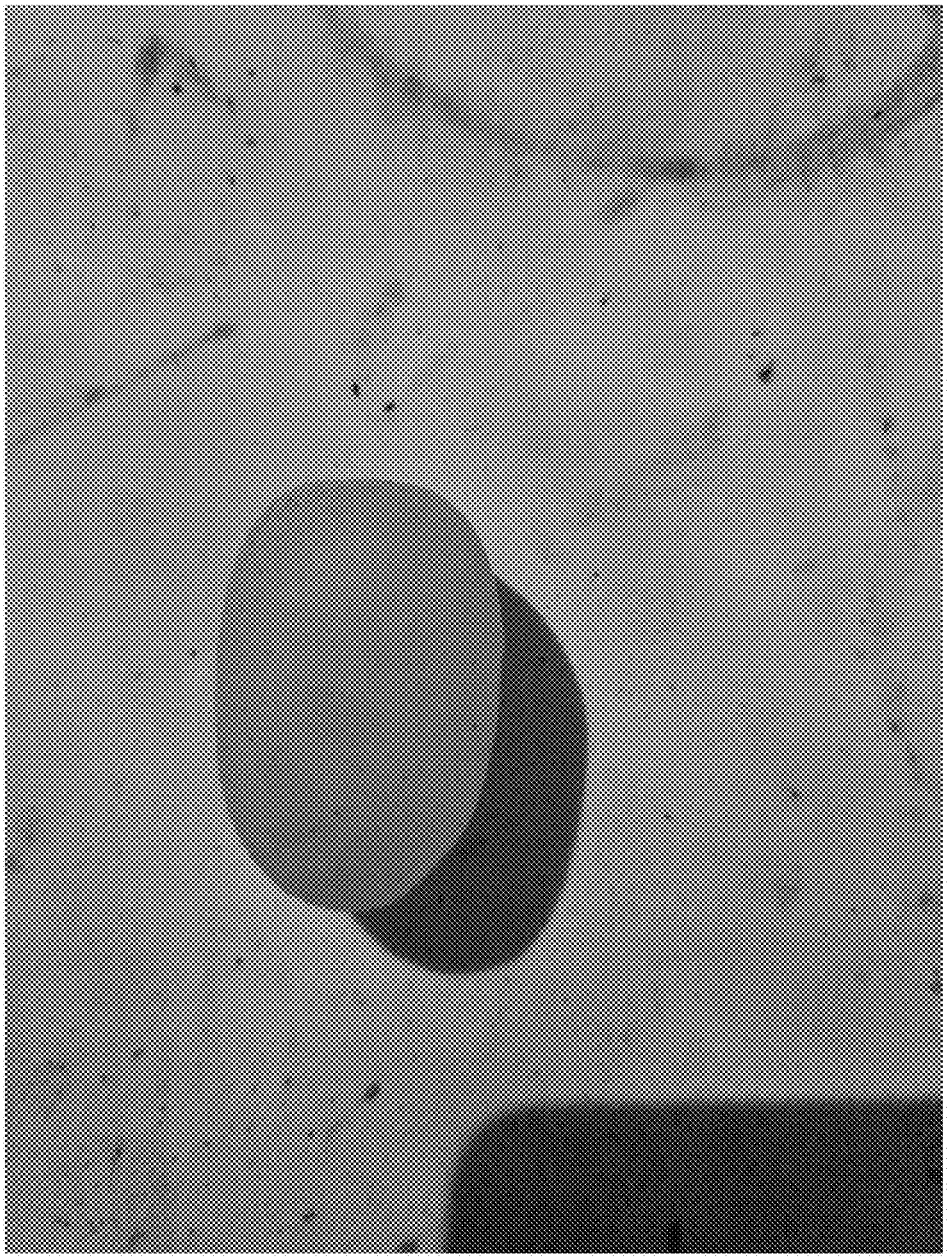

FIG. 3—shows a typical berry of 'Big Bear'.

Figure 4:
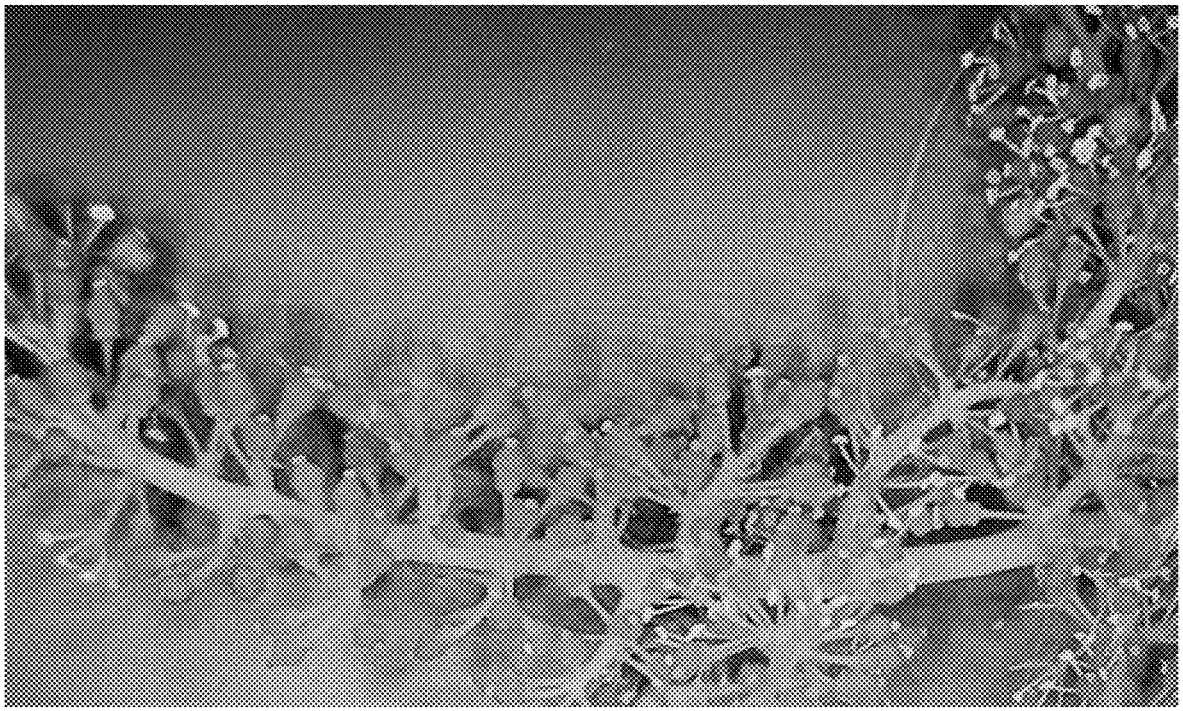

FIG. 4—shows a typical inflorescence of 'Big Bear'.

DETAILED MORPHOLOGICAL DESCRIPTION

The new *Vitis vinifera* 'Big Bear' has not been observed under all possible environmental conditions. The phenotype of the new variety may vary with variations in environment such as temperature, light intensity, day length, soil or pruning without any change in the genotype of the Grapevine plant.

The afore mentioned photographs, together with the following observations, measurements and values describe plants of 'Big Bear' as grown in the vineyard in Karmei Yossef, Gezer region in HaShephelah, Israel—under conditions which closely approximate those generally used in commercial practice.

Unless otherwise stated, the detailed morphological description includes observations, measurements and values taken from 2012 to 2024 and based on 10-year-old 'Big Bear' plants grown in the vineyard in Karmei Yossef, Gezer region in HaShephelah, Israel. Quantified measurements are expressed as an average or a range of measurements taken from ten plants of 'Big Bear'. The measurements of any individual plant, or any group of plants, of the new variety may vary from the stated average or range.

Color references are made to The Royal Horticultural Society Colour Chart (R.H.S.), edition 1986, except where general colors of ordinary significance are used. Color values were taken under daylight conditions in full sunlight in Karmei Yossef, Gezer region in HaShephelah, Israel.

All the plants of 'Big Bear', insofar as they have been observed, have been consistent in all the characteristics described below.

Classification:

*Botanical.*—*Vitis vinifera.*

Parentage:

*Female or seed parent.*—*Vitis vinifera* 'H 1352' (unpatented).

*Male or pollen parent.*—*Vitis vinifera* 'H 8351' (unpatented).

Propagation: Rooted cuttings.

Growing conditions:

*Light intensities.*—Full sunlight.

*Temperature.*—During the day, grown in range of 10° C. to 35° C., and during the night grow in range of 0° C. to 25° C. Located at an elevation of 238.79 meters (783.43 feet) above sea level. Karmei Yosef has a Mediterranean, hot summer climate (Classification: Csa). The district's yearly temperature is 23.04° C. (73.47° F.). It is 0.35% higher than Israel's averages. Karmei Yosef typically receives about 16.8 millimetres (0.66 inches) of precipitation and has 40.43 rainy days (11.08% of the time) annually. Karmei Yosef, Central District, Israel Climate Weather: 16.73° C./62.11° F, Wind SW at 2.57 km/h, 61% Humidity, 0.15% chance of rain.

TABLE 3

Karmei Yosef Climate Summary January - December

| Kamei Yossef yearly average of temperature and precipitation | JAN | FEB | MAR | APR |
|---|---|---|---|---|
| Daily mean temperature | 12° C. (53° F.) | 13° C. (55° F.) | 15° C. (59° F.) | 19° C. (66° F.) |
| Average precipitation mm (inches) | 48 (1.9) | 44 (1.7) | 39 (1.5) | 19 (0.8) |
| **Kamei Yossef yearly average of temperature and precipitation** | **MAY** | **JUN** | **JUL** | **AUG** |
| Daily mean temperature | 23° C. (74° F.) | 25° C. (77° F.) | 27° C. (82° F.) | 28° C. (82° F.) |
| Average precipitation mm (inches) | 7 (0.3) | 2 (0.1) | 1 (0.0) | 1 (0.0) |
| **Kamei Yossef yearly average of temperature and precipitation** | **SEP** | **OCT** | **NOV** | **DEC** |
| Daily mean temperature | 26° C. (80° F.) | 23° C. (74° F.) | 19° C. (66° F.) | 15° C. (59° F.) |
| Average precipitation mm (inches) | 1 (0.0) | 14 (0.6) | 25 (1.0) | 33 (1.3) |

Fertilization: A balanced fertilizer with a level of NPK 25.7.30 from bud burst in January till February.

Growth regulators: Dormex® to stimulate bud wakening and gibberellin to enlarge berry size.

Plus microelements: 1.5 L. in each 5 m3 of water.

Pruning: As in commercial practice: 4 long young shoots each with 12 eyes.

Training: Y trailing cordon. The size and overall shape of Grapevine plants essentially depend on pruning and spacing. 'Big Bear' was pruned, creating a plant which is trailing horizontally with three, four or five main vines. When the plants are freely grown, the size and the shape assumed by the plants are typical of *Vitis vinifera*.

Plant:

*Age*.—Observed plants were 10 years old.

*Time of bud burst*.—Mid-season.

*Young shoot*.—Openness of tip: closed. Density of prostrate hairs on tip: absent or very sparse. Anthocyanin coloration of prostrate hairs on tip: absent or very sparse. Color: green — RHS 144A. Length: up to 20 cm. Diameter: about 1 mm.

*Young leaf*.—Color of upper side of leaf blade: medium green — RHS 141C. Color of lower side of leaf blade: light green — RHS 141 D. Anthocyanin coloration: absent. Density of hairs between main veins on lower side of blade: absent or very sparse. Glossiness of upper side: medium. Glossiness of lower side: medium. Length of internode: up to 10 cm. Length: about 3 cm. Width: about 2 cm. Shape: pentagonal. Apex: acute. Margin: entire. Base descriptors: shape obtuse. Texture (both surfaces): glabrous.

*Shoot*.—Color of dorsal side of internode: light green — RHS 141 D with strong anthocyanin over color. Color of ventral side of internode: light green — RHS 141 D. Color of dorsal side of node: light green — RHS 141D with strong anthocyanin over color. Color of ventral side of node: light green — RHS 141 D. Color designation for the anthocyanin coloration: dark reddish brown — RHS 181 A. Density of erect hairs on internodes: absent or very sparse. Consecutive tendrils: at all modes. Length of tendril: up to 20 cm.

*Tendril*.—Number per shoots: up to 15. Diameter: about 2 mm. Texture: smooth. Color: light yellow green — RHS 145 B.

*Inflorescence*.—Length: about 16-20 cm. Width: 7-9 cm. No. of side branches: about 7-12. Attitude of side branches: semi-upright. Length of longest side branch: about 4-5 cm. Diameter of side branch: less than 1 mm. Texture of side branch: smooth. Color of side branch: light yellow green — RHS 146 D. Thickness of main axis: about 3-4 mm. Green color of main axis: light yellow green — RHS 146 D. Anthocyanin coloration of main axis: absent. Pubescence of main axis: absent.

*Flower*.—Sexual organs: complete.

*Bud*.—Length: pin-head. Diameter: pin-head. Texture: smooth. Color: light green — RHS 145 C.

*Full bloom*.—Mid April.

*Pedicel*.—Length: about 1 mm. Thickness: about 0.5 mm. Green color: light green — RHS 145 C. Pubescence: absent/glabrous.

*Stamen*.—Number: 5. Length of filament: about 2-3 mm. Thickness of filament: minuscule. Pubescence of filament: absent. Surface: smooth. Color: light green — RHS 145 C.

*Petals*.—Number: five. Shape: invisible. Length: minuscule. Width: minuscule. Apex: fused. Margin: inconspicuous. Base descriptors: fused. Texture: smooth. Color: green — RHS 144 A.

*Sepals*.—Invisible.

*Anther*.—Shape: transverse elliptic elongated. Length: minuscule. Color: Light green — RHS 145 C.

*Pollen*.—Color: yellow — RHS 150 B. Amount of pollen produced: abundant.

*Ovary*.—Shape: elliptic. Color: green — RHS 144 A. Length: about 1-2 mm. Diameter: about 1 mm. Surface: smooth.

*Style*.—Length: minuscule.

*Stigma*.—Size: minuscule. Color: yellow — RHS 150 B.

*Mature leaf*.—Size of blade: medium. Blade length: about 12 cm. Blade width: about 12 cm. General shape of blade: circular. Green color of upper side: dark green RHS 141 A. Green color of lower side: medium green RHS 141 C. Glossiness of upper side: strong. Glossiness of lower side: medium. Profile in cross section: flat. Blistering of upper side: absent. Number of lobes: 5. Central lobe length: about 9 cm. Central lobe width: about 7 cm. Upper lateral lobe length: about 9 cm. Upper lateral lobe width: about 8 cm. Pubescence of veins on upper side: absent or very sparse. Pubescence of veins on lower side: absent or very sparse. Green color of veins on upper side: very light green — RHS 144 D. Green color of veins on lower side: very light green — RHS 144 D. Anthocyanin coloration of veins on upper side: absent. Anthocyanin coloration of veins on lower side: absent. Depth of upper lateral sinuses: very shallow. Arrangement of lobes of petiole sinus: slightly overlapping. Petiole sinus limited by veins: none. Length of distal tooth: about 2 mm. Width of distal tooth: about 2 mm. Ratio length/width of distal tooth: 1. Shape of teeth: both sides convex. Anthocyanin coloration of main veins on upper side of blade: absent or very sparse. Density of hairs between veins on upper side of blade: absent or very sparse. Density of hairs between veins on lower side of blade: absent or very sparse. Length of petiole compared to middle vein: moderately shorter.

*Petiole*.—Length: 5-6 cm. Thickness: about 4 mm. Green color of upper side: dark green — RHS 141 A. Anthocyanin coloration of upper side: absent or very sparse. Anthocyanin coloration of lower side: absent or very sparse. Green color of lower side: very light green — RHS 144 D. Pubescence: absent or very low.

*Fruit*.—Time of beginning of berry ripening: early to mid-season.

*Bunch*.—Length (peduncle excluded): 18-28 cm. Width (peduncle excluded): 10-12 cm. General shape (peduncle excluded): triangular. Weight (peduncle excluded): 800-1200 g. Density: dense. Length of peduncle: 4-5 cm.

*Peduncle*.—Diameter: 1-2 mm. Texture: smooth. Color: very light green — RHS 144 D.

*Berry*.—Length: about 30 mm. Diameter: about 22 mm. Shape: broad ellipsoid. Color of skin (without bloom): between light yellowish green — RHS 145 B and light green — RHS 145 C. Ease of pedicel detachment: moderately easy. Length of pedicel: 6-10 mm. Thickness of pedicel: about 1 mm. Color of pedicel: light yellow green — RHS 144 C. Texture of pedicel: smooth. Thickness of skin: thin. Flesh anthocyanin coloration: absent. Flesh color: light Yellowish green RHS 145 C. Firmness of flesh: moderately firm. Juiciness of flesh: juicy. Total soluble solids: 16-20° Bx. Acidity: 0.4-0.8 pH. Particular flavour: sometimes slightly muscat. Formation of seeds: rudimentary. Number of berries per primary bunch: 80-120.Sweetness: very sweet (Total Soluble Solids (T.S.S.)) 16-22%, (Brix percentage): 20° Brix.

*Woody shoot*.—Main color (without bloom): medium brown — RHS 164 A. Relief of surface: ribbed. Length: larger than 10 cm depending on pruning. Diameter: 4-7 mm.

Disease resistance: Low susceptibility to Grape Sour Rot.

Pest resistance: Relative resistant to *Drosophila melanogaster*.

Usage: Table grape.

Shipping quality: Mostly packed in 5-10 cartons.

Storage life and productivity: The grapes can be easily stored in the refrigerator for over a month. Productivity is 50-60 kg for plants in average conditions and on adult plants.

I claim:

1. A new and distinct Grapevine plant of *Vitis vinifera* named 'Big Bear', as herein described in the specification.

* * * * *